(12) United States Patent
Sohn et al.

(10) Patent No.: US 9,732,014 B2
(45) Date of Patent: Aug. 15, 2017

(54) METHOD OF PRODUCING ALKYLAROMATIC COMPOUNDS USING AROMATIC COMPOUND FROM CATALYST REGENERATION

(71) Applicant: UOP LLC, Des Plaines, IL (US)

(72) Inventors: Stephen W. Sohn, Arlington Heights, IL (US); Shuguang Zhang, Wilmette, IL (US); Priyesh Jayendrakumar Jani, Haryana (IN); Soumendra M. Banerjee, New Delhi (IN)

(73) Assignee: UOP LLC, Des Plaines, IL (US)

( * ) Notice: Subject to any disclaimer, the term of this patent is extended or adjusted under 35 U.S.C. 154(b) by 253 days.

(21) Appl. No.: 14/200,693

(22) Filed: Mar. 7, 2014

(65) Prior Publication Data

US 2015/0251974 A1 Sep. 10, 2015

(51) Int. Cl.
    *C07C 2/66* (2006.01)
    *C07C 5/27* (2006.01)
    *C07C 6/12* (2006.01)

(52) U.S. Cl.
    CPC .............. *C07C 2/66* (2013.01); *C07C 5/2775* (2013.01); *C07C 6/126* (2013.01); *Y02P 20/584* (2015.11)

(58) Field of Classification Search
    CPC ...... C07C 5/2775; C07C 6/126; C07C 15/107
    See application file for complete search history.

(56) References Cited

U.S. PATENT DOCUMENTS

| | | | |
|---|---|---|---|
| 5,491,271 A * | 2/1996 | Marinangeli | C07C 2/66 502/20 |
| 6,069,285 A | 5/2000 | Fritsch et al. | |
| 6,740,789 B1 * | 5/2004 | Bozzano | C07C 2/66 585/323 |
| 7,199,068 B2 | 4/2007 | Winder et al. | |
| 7,217,850 B2 | 5/2007 | Guillon et al. | |
| 7,576,247 B2 | 8/2009 | Sohn et al. | |
| 7,642,389 B2 | 1/2010 | Sohn et al. | |
| 7,652,181 B1 | 1/2010 | Schmidt et al. | |
| 7,652,182 B2 | 1/2010 | Sohn et al. | |
| 2008/0194895 A1 * | 8/2008 | Sohn | C07C 2/66 585/435 |

FOREIGN PATENT DOCUMENTS

| | | |
|---|---|---|
| CN | 1131107 C | 12/2003 |
| WO | WO 2005/118514 A1 | 12/2005 |

OTHER PUBLICATIONS

Han et al., "Synthesis of linear alkylbenzene in a novel liquid-solid circulating moving bed reactor," Chinese Journal of Chemical Engineering (2004), 12(3), 379-383.
Wilkinson, Sophie L., "Petresa cuts lab impurities," Chemical Week (1989), 145 (8), 14-15.
Han et al., "Synthesis of linear alkylbenzene using TH-06 catalyst . . . ," Petrochemical Technology (1999), 28(11), 734-737.
Imai et al., "The UOP/CEPSA detal process," Science and Technology in Catalysis 1994 (1995), vol. 92, 339-342.
Han et al., "Synthesis of linear alkylbenzene catalyzed by H-zeolite," Applied Catalysis A: General (2002), 238(1) 99-107.

* cited by examiner

*Primary Examiner* — Sharon Pregler
*Assistant Examiner* — Alyssa L Cepluch

(57) ABSTRACT

A process for producing alkylaromatic compounds is described. The process involves utilizing at least a portion of the aromatic compound used to regenerate the alkylation catalyst in a spent alkylation reaction zone as a reactant in the active alkylation reaction zone.

20 Claims, 2 Drawing Sheets

US 9,732,014 B2

METHOD OF PRODUCING ALKYLAROMATIC COMPOUNDS USING AROMATIC COMPOUND FROM CATALYST REGENERATION

BACKGROUND OF THE INVENTION

Linear alkylbenzenes (LAB) are compounds that have significant commercial importance. Linear alkylbenzene sulfonate (LAS) compounds made by sulfonation of linear alkylbenzene are used in the manufacture of detergents and other products. Because linear alkylbenzenes are more easily biodegradable than branched alkylbenzenes, linear alkylbenzenes have essentially replaced branched alkylbenzenes in detergents and other products. In particular, linear alkylbenzenes with long alkyl chains, such as chains having about 10 to about 14 carbons, are commonly used. However, linear alkylbenzenes with longer chains and with shorter chains also are commercially important.

Linear alkylbenzenes often are made by alkylation of benzene with olefins. Positional isomers, such as 2-phenyl, 3-phenyl, 4-phenyl, 5-phenyl, and the like, result from this alkylation of benzene with long chain olefins. The distribution of the phenyl along the alkyl chain produces different products.

Historically, linear alkylbenzenes have been manufactured commercially using Friedel-Crafts condensation employing catalysts such as aluminum chloride, or by using strong acid catalysts such as hydrogen fluoride, for example, to alkylate benzene with olefins. In 1995, a solid bed alkylation process, the Detal™ process, using a solid non-corrosive acid catalyst was introduced.

In processes using solid alkylation catalysts, the alkylation catalysts need to be regenerated periodically to remove the heavy alkylbenzene deposited on the catalyst during the process cycle. Regeneration is usually accomplished by washing the catalyst with benzene at a specified temperature.

A need exists for improved methods of making alkylaromatic compounds and improved methods for regenerating alkylation catalysts.

SUMMARY OF THE INVENTION

One aspect of the invention is a process for producing alkylaromatic compounds. In one embodiment, the process includes contacting an aromatic compound and an olefin in an alkylation reaction zone under alkylation conditions in the presence of an alkylation catalyst to produce an alkylation product containing monoalkylaromatic compounds, dialkylaromatic compounds, and unreacted aromatic compound; separating the alkylation product in a separation zone into an unreacted aromatic fraction and a fraction containing the monoalkylaromatic compounds and the dialkylaromatic compounds; regenerating a spent alkylation reaction zone by passing an aromatic compound stream through the spent alkylation zone at a regeneration temperature above an alkylation temperature to provide a regeneration aromatic compound stream; and introducing at least a portion of the regeneration aromatic compound stream into the alkylation zone, a transalkylation zone, or both, the regeneration aromatic compound stream being at the alkylation temperature.

DETAILED DESCRIPTION OF THE INVENTION

The aromatic compound used in the alkylation process can be any suitable aromatic compound, including, but not limited to, benzene, toluene, ethylbenzene, xylenes, or combinations thereof. Benzene is the most commonly used aromatic compound. Consequently, benzene will be used for ease of discussion.

Alkylbenzenes, also known as phenyl alkanes, are important for many different products. When the alkyl group has 8 to 20 carbon atoms, among the common usages is in the formation of detergents. Alkylbenzenes are an intermediate product used to form alkylbenzene sulfonates, which are surfactants that form the basis of many detergents. The alkylbenzene sulfonates are known to exhibit different physical properties based upon the position of the aromatic group on the alkyl chain. In the production of alkylbenzene sulfonates, the intermediate product alkylbenzenes with 2-phenyl isomer content in the range from about 25 to 40 percent are particularly desired.

Figure 1:
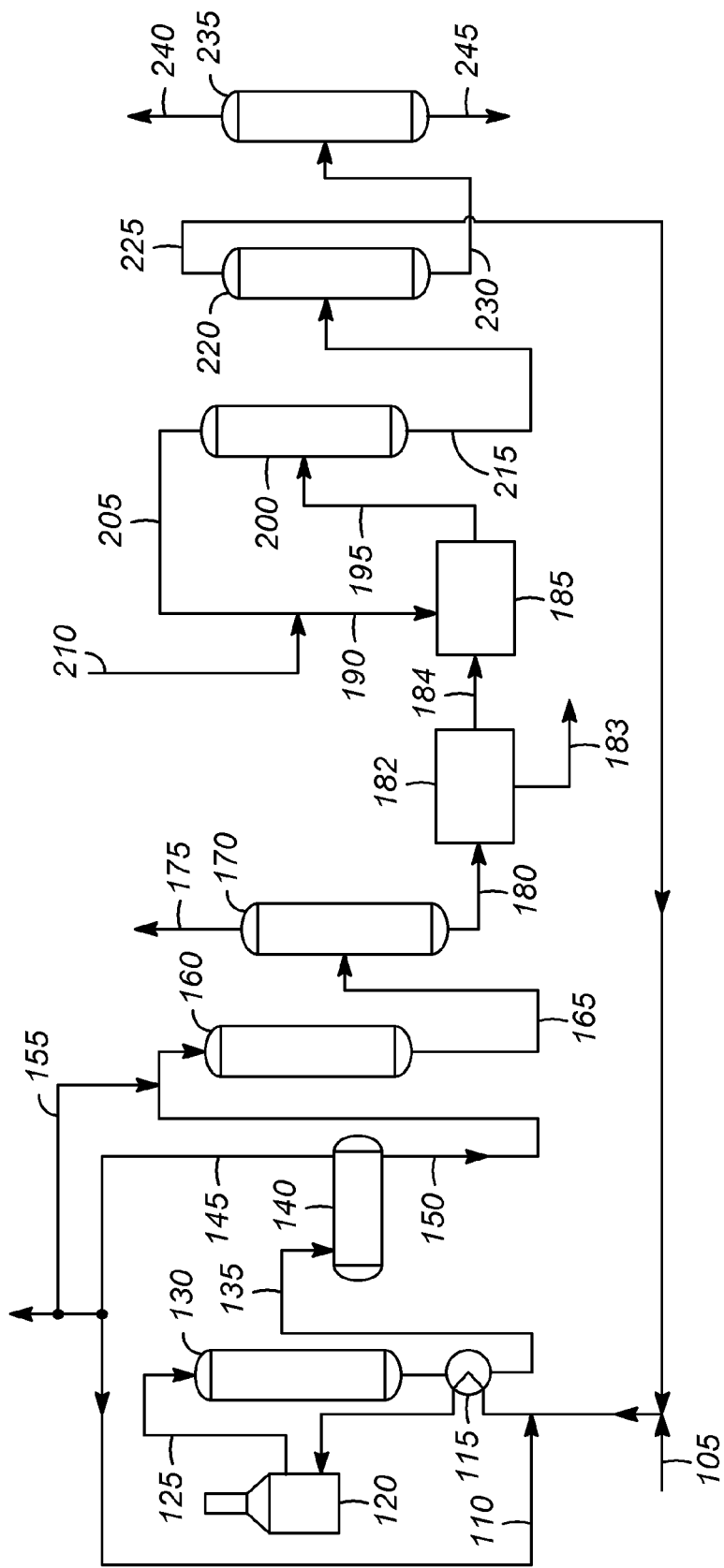
FIG. 1 is an illustration of one embodiment of a process for making alkylbenzenes.

Integrated processes for producing LABs using solid alkylation catalysts have been developed. One example of an integrated process is shown in FIG. 1 which includes a dehydrogenation process, followed by a selective catalytic hydrogenation process, and an alkylation process. A paraffin feed 105 is mixed with hydrogen 110 and sent through heat exchanger 115 and charge heater 120. The heated stream 125 is sent to dehydrogenation zone 130. The dehydrogenation effluent 135 exchanges heat with the feed 105 and hydrogen 110 in heat exchanger 115. The dehydrogenation effluent 135 is then sent to a separator 140 and separated into a hydrogen gas stream 145 and liquid stream 150. The liquid stream 150 is mixed with hydrogen 155 sent to a selective hydrogenation zone 160 where any diolefins are hydrogenated to monoolefins. The effluent 165 from the selective hydrogenation reactor 160 is sent to a stripper 170 where light ends 175 are removed. The bottoms stream 180 from the stripper 170 is sent to an aromatics removal zone 182 where aromatics 183 are removed. The treated stream 184 is sent to the alkylation zone 185 where it is mixed with a benzene stream 190. The effluent 195 from the alkylation zone 185 is sent to a benzene distillation column 200. The benzene overhead stream 205 can be mixed with fresh benzene 210 to form the benzene stream 190. The bottoms stream 215 from the benzene column 200 is sent to a paraffin distillation column 220. The paraffin overhead stream 225 is mixed with paraffin feed 105 and sent to the dehydrogenation zone 130. The bottoms stream 230 from the paraffin column 220 is sent to an alkylbenzene distillation column 235 where it is separated into an overhead stream 240 containing the monoalkylbenzene and a bottoms stream 245 containing heavy alkylbenzene (e.g., dialkylbenzene). The overhead stream 240 can be further processed, for example, in a finishing column (not shown), if desired. The bottoms stream of heavy alkylbenzene can be further processed, for example, in a transalkylation unit (not shown) with benzene, to further enhance the yield of monoalkylbenzene, if desired.

In existing processes, two alkylation reactors are typically operated simultaneously, one in the alkylation process cycle and one in a regeneration cycle. The cycle time is generally about 24 hrs for both the alkylation process cycle and the regeneration cycle. The spent alkylation reactor is heated from the alkylation temperature (typically 80° C. and about 200° C., most usually at a temperature not exceeding about 175° C., or about 100° C. to 160° C., or about 120° C. to about 150° C., or about 130° C. to about 140° C.) to the regeneration temperature (typically about 160° C. to about 250° C., or about 180° C. to about 250° C.), which takes about 8 hr. It is maintained at the regeneration temperature for a period of time, typically about 8 hr. Then the reactor is cooled down to the alkylation temperature, which generally takes about 8 hr.

Regeneration typically takes place at a pressure in the range of about 1.300 MPa(g) to about 7.000 MPa(g), or about 2.758 MPa (400 psig) to about 4.137 MPa (600 psig), or about 3.44 MPa (500 psig). The system is operated so that the benzene is in the liquid phase at the operating temperatures.

After regeneration, the benzene stream can be sent back to the benzene column for purification and re-use. However, this increases the amount of benzene circulated in the system, increasing the cost of production. Alternatively, the stream can be sent to the aromatics removal unit and used as a desorbent. However, this cannot be done if the stream contains impurities which will impede the performance of the aromatics removal unit, such as water.

In the present invention, at least a portion of the benzene regeneration stream is routed to the alkylation reactor and/or the transalkylation reactor. In some embodiments, the entire stream is sent to the alkylation reactor and/or the transalkylation reactor. A portion can also be sent to the benzene column, if desired.

In some current processes, about two thirds of the benzene used for alkylation comes from the aromatics removal unit and one third is from the benzene column. The use of regeneration benzene for alkylation can partially or completely replace the use of fresh benzene in the alkylation reactor and reduce the amount of benzene from the aromatics removal unit. The regeneration benzene can also be used for transalkylation, reducing or eliminating the use of fresh benzene there as well.

The regeneration effluent stream is almost 99% benzene after the initial 6 hours of flushing, and it contains trace amounts of linear alkylbenzene and heavy alkylbenzene (e.g., less than 0.5 wt %) removed during the high temperature regeneration.

Figure 2:
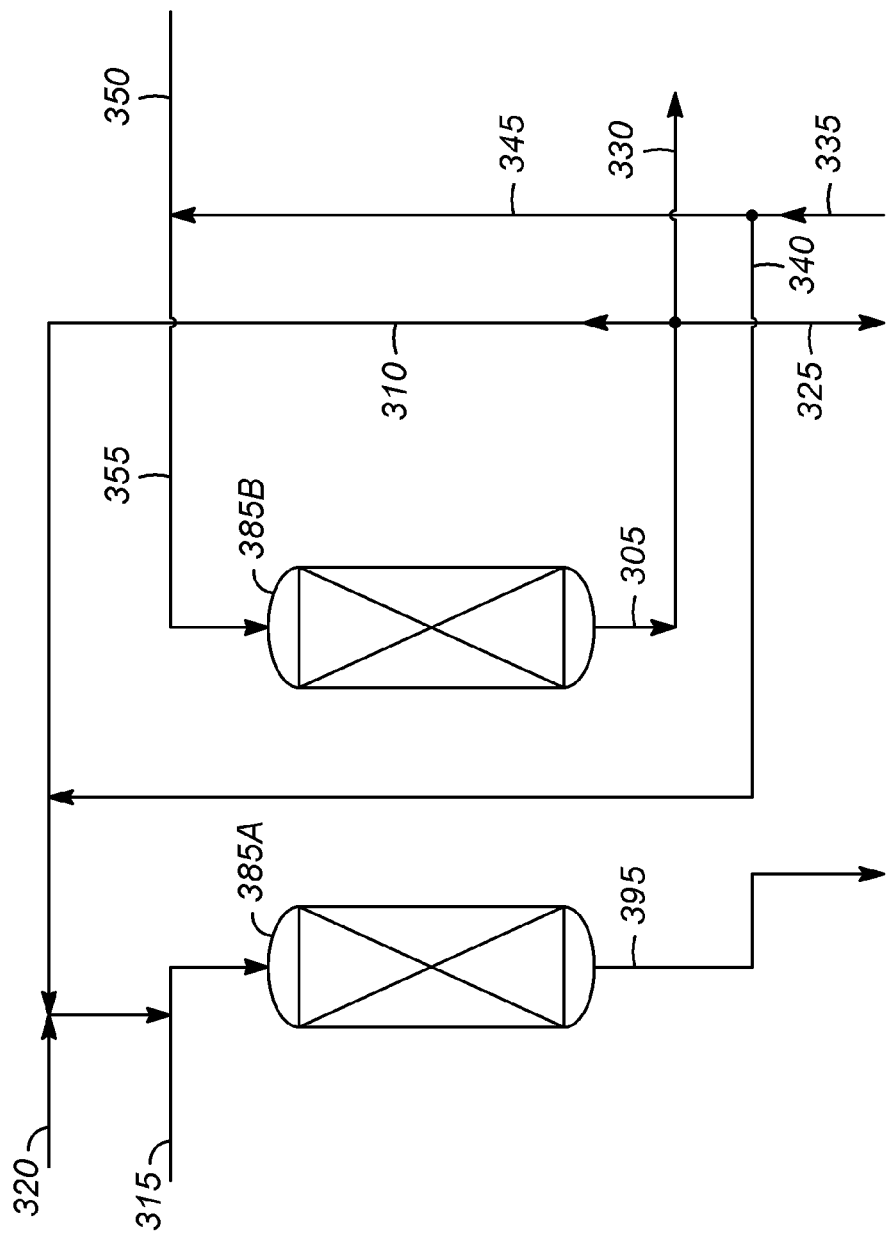
FIG. 2 is an illustration of one embodiment of a process for regenerating alkylation catalysts.

In one embodiment shown in FIG. 2, a portion 310 of the regeneration benzene effluent 305 from the regeneration reaction zone 385B is mixed with the olefin feed 315 to the alkylation reaction zone 385A which is running the alkylation cycle.

Olefin feed 315 can come from the process described above in FIG. 1. In this case, olefin feed 315 would include unreacted paraffins from the dehydrogenation reaction. Other sources of the olefin feed 315 include, but are not limited to, $C_{10}$ to $C_{12}$ alpha olefins produced from ethylene in a linear alpha olefins process, and the olefin/paraffin product of a gas to liquid process.

Effluent 395 from the alkylation reaction zone is sent to the benzene column for separation, as described above in FIG. 1.

The portion 310 of regeneration benzene effluent 305 can be mixed with the feed 315 before it goes to a charge heater (not shown). By using the portion 310 of regeneration benzene effluent 305, the amount of fresh benzene 320 from the benzene column can be reduced or eliminated.

In some embodiments, a portion 325 of the regeneration benzene effluent 305 can be sent to the transalkylation reaction zone. In some embodiments, a portion 330 of the regeneration benzene effluent 305 can be sent to the benzene column for separation.

The largest portion of the regeneration benzene effluent is generally sent to the alkylation reaction zone, although this is not required. The portion of the regeneration benzene effluent sent to the alkylation reaction zone 385A is typically about 30 wt % or more, or about 40 wt % or more, or at least about 50 wt % or more, or about 60 wt % or more, or about 70 wt % or more, or about 80 wt % or more, or about 90 wt % or more. In some embodiments, all of the regeneration benzene effluent 305 is sent to the alkylation reaction zone 385A.

Generally, the remainder of the regeneration benzene effluent is sent to the transalkylation reaction zone and/or the benzene column. Typically, at least about 50 wt % or more of the remainder of the regeneration stream is sent to the transalkylation reaction zone. For example, if 60 wt % of the regeneration benzene effluent is sent to the alkylation zone, at least 20 wt % (50 wt % of the 40 wt % remainder) would be sent to the transalkylation reaction zone.

In some embodiments with a 30:1 benzene:olefin molar ratio in the alkylation reaction zone with an aromatics removal zone, the regeneration benzene can supply all of the the benzene to the alkylation reaction zone and all of the benzene to the translakylation zone.

Whatever is left (if anything) after the portions of the regeneration benzene effluent are sent to the alkylation reaction zone and transalkylation reaction zone can be sent to the benzene column. The amount of regeneration benzene effluent sent to the benzene column is desirably less than 50 wt % or less than 40 wt %, or less than 30 wt %, or less than 20 wt %, or less than 10 wt % of the total regeneration benzene effluent. Reducing the amount of regeneration benzene effluent sent to the benzene column reduces the operating cost of process.

Benzene stream 335 comes from the aromatics removal unit. A portion 340 of the benzene 335 can be supplied to the alkylation reaction zone 385A. The use of the portion 310 of regeneration benzene effluent 305 in the alkylation reaction zone 385A can reduce or eliminate the portion 340 of the benzene 335 needed for the alkylation process.

A portion 345 of the benzene 335 can be mixed with benzene 350 from the benzene column to form benzene stream 355 which is fed to the regeneration zone 385B during the regeneration cycle. This will reduce the net regeneration benzene needed, and consequently will reduce the energy requirement of the benzene column.

For a single feed configuration, mixing 50 wt % of regeneration benzene effluent 305 with reactor feed 315 will reduce the fresh benzene 320 to olefin molar ratio.

The process will generate some additional heavy alkylbenzene during the alkylation process cycle due to trace amounts of linear alkylbenzene and heavy alkylbenzene which are already present in the regeneration benzene effluent 305. However, the overall process specification would remain unchanged as the process will be operated at higher benzene:olefin molar ratio.

Testing in the pilot plant has demonstrated that ZDA-2 catalyst (available from UOP LLC) made almost half of the heavy alkylbenzene compared with DA-114 catalyst (available from UOP LLC) at the same benzene:olefin molar ratio (3% for ZDA-2 compared with 6% for DA-114). Consequently, the overall heavy alkylbenzene specification will remain the same by mixing additional regeneration benzene effluent in the feed.

The additional heavy alkylbenzene generated during the process could be converted back to linear alkylbenzenes in the transalkylation reactor.

The amount of heavy alkylbenzene in the product stream could be controlled by maintaining a regeneration benzene effluent flow into the alkylation process feed.

In some embodiments, the process allows the reduction of the benzene:olefin molar ratio in the feed from the current process by allowing recycling of the regeneration benzene effluent from the regeneration zone to the active alkylation reaction zone.

In some embodiments, the total reactor effluent to the benzene column is reduced, which decreases the energy requirement for the benzene column.

In some embodiments, the regeneration benzene effluent required for the transalkylation reaction zone is small, so the recycling of the regeneration benzene effluent will not affect the flow to the alkylation reaction zone.

In some embodiments, the unconverted olefins that are flushed out in the initial hours (e.g., about 4 to 6 hrs) of the regeneration process can be recycled to a reaction zone where they are converted to products by mixing with the alkylation reaction zone feed. This can avoid olefin breakthrough during the reaction.

The olefin feed to the alkylation zone coming from a dehydrogenation process will typically have a concentration of between about 9 wt % and about 15 wt % olefins and between about 85 wt % to about 91 wt % paraffins.

The aliphatic feedstock used in the alkylation processes of this invention contains aliphatic mono-olefin of 8 to 20, or 8 to 18, or 8 to 17 carbon atoms per molecule. The feed is typically limited to 4 consecutive carbon numbers at any particular time. The aliphatic olefin is usually a mixture of olefins having different molecular weights. The olefin may be an alpha-olefin or comprise a mixture of olefin isomers. In most instances, the positioning of the olefinic bond in the molecule is not critical as most solid alkylation catalysts have been found to promote migration of the olefinic bond.

For commercial processes, other components may be present in the aliphatic feedstock with the olefin-containing aliphatic compound. These other components may comprise paraffins of, for example, 9 to 17 carbon atoms per molecule which can act as heat sinks to maintain the desired temperature in the alkylation reaction zone. However, such amounts of paraffin are not critical to the processes of this invention, and aliphatic feedstocks having an essential absence of paraffins can be used. If paraffins are not present, then another component that can act a heat sink and remains unreacted under the process conditions will need to be present to maintain the LAB linearity and 2-phenyl content, if that is needed for the particular application.

In some embodiments, a multi-bed alkylation reaction zone and a split feedstream for controlling the 2-phenyl content in an alkylbenzene product stream are employed. This arrangement is described in U.S. Pat. No. 8,389,787, which is incorporated herein. The split-bed design of U.S. Pat. No. 8,389,787 is optimized for feedstock utilization and energy consumption.

The aromatic compound and the olefin are reacted under alkylation conditions in the presence of a solid alkylation catalyst. These alkylation conditions generally include a temperature in the range between about 80° C. and about 200° C., as discussed above. Typically, as the catalyst ages, the temperature of the alkylation is increased to maintain desired activity. The alkylation is an exothermic reaction, and thus in a substantially adiabatic reactor, the effluent is at a higher temperature than that of the feed. A substantially adiabatic reactor is one where the increase in temperature of the effluent over that of the feed accounts for at least about 75 percent of heat generated by the reactions in the reaction zone.

Typically, the temperature within a reaction zone is maintained within a suitable range by providing a large excess of aromatic compound to the reaction zone to absorb heat. Where the aliphatic feedstock contains paraffins, the paraffins also serve to absorb heat from the exothermic reactions. High exothermic temperatures during the alkylation can result in negative effects not only in terms of catalyst deactivation and loss in linearity of the LAB due to increased olefin isomerization to non-linear olefins, but also in terms of product quality degradation, especially skeletal isomerization, and, in particular, skeletal isomerization of the olefin.

Since the alkylation is typically conducted in the presence of a liquid phase, and preferably in either an all-liquid phase or at supercritical conditions, pressures must be sufficient to maintain reactants in the liquid phase. The requisite pressure necessarily depends upon the olefin and temperature, but normally is in the range of about 1.300 to 7.000 MPa(g).

In some embodiments, alkylation of benzene by the olefins is conducted in a continuous manner using three or more catalyst beds in flow series. For purposes herein, a catalyst bed is termed a reaction zone whether in the same or a separate vessel from another bed. Each reaction zone has an inlet region and an outlet region. The reactants may be in admixture prior to entering the inlet region of the reaction zone, or they may be individually introduced and mixed in the reaction zone.

The catalyst may be used as a packed bed, a moving bed, or a slurry bed. The feed to the reaction zone may be passed either upflow or downflow, or even horizontally as in a radial bed reactor; however, the flows of the aromatic compound and olefin are co-current. In one desirable variant, olefin may be fed into several discrete points within the reaction zone. The feed mixture, that is, aromatic compound and aliphatic feedstock to a reaction zone, is often provided at an overall liquid hourly space velocity (overall LHSV) between about 0.3 and about 6 or 10 $hr^{-1}$, and most frequently between about 0.4 and 6 $hr^{-1}$ depending upon, e.g., alkylation temperature and the activity of the catalyst. The overall LHSV is determined from the LHSV's of each of the beds. The reciprocal of the overall LHSV is the sum of the reciprocals of the LHSV of each of the beds in series.

It is usually desired that sufficient residence time in the reaction zone be used such that at least about 90, or at least about 95, or at least about 98, and often at least about 99.5, mass percent of the olefin fed to a reaction zone is reacted in that reaction zone.

Any suitable solid alkylation catalyst may be used in the present invention, provided that the requirements for conversion, selectivity, and activity are met. Typically, the catalysts are acidic. Preferred alkylation catalysts comprise zeolites having a zeolite framework type selected from the group consisting of FAU, MOR, MTW, and NES. Suitable zeolites include mordenite, ZSM-4, ZSM-12, ZSM-20, ZSM-38, offretite, gmelinite, beta, NU-87, UZM-8, MCM-22, MCM-36, MCM-49, zeolite Y, zeolite X, and gottardite. The MOR, MWW, FAU, NES, and other zeolite framework types are described in Ch. Baerlocher, W. M. Meier and D. H. Olson, "Atlas of Zeolite Framework Types," 5th Ed., Elsevier: Amsterdam, 2001, herein incorporated by reference. The FAU and UZM-8 molecular sieves may have any convenient particle size. Often the particle sizes of the molecular sieves range upwards of 5 microns or more in major dimension, for example, about 50 to 5000 nanometers in major dimension. Particle sizes in the lower portion of the range are sometimes preferred as the coproduction of heavies may be reduced. Major particle dimensions of less than about 500, e.g., from about 50 to 300, nanometers are often desirable. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964B1 and 6,617,481B1.

Newer alkylation catalysts can also be used in this process. For example, one such catalyst comprises a mixture of two types of zeolitic materials, where the zeolites are mixed and produced to have two zeolites within a single catalyst pellet. With the new catalysts, the first zeolite is also characterized by its acidity, wherein the acidity is characterized by having less than 70% of $NH_3$ desorption off the zeolite at temperatures greater than 400° C. The $NH_3$-TPD experimental procedure comprises: calibration of the $NH_3$-TPD system with 5 injections of 0.2 cc pulses of $NH_3$ at 2 minute intervals into a flow of UHP grade helium at 40 cc/minute. The data collected from the Thermal Conductivity Detector is integrated and used to calibrate the detector response to a known quantity of $NH_3$. An equilibrated sample, for moisture content is weighed at approximately 250 mg and placed in the reactor. The sample is pretreated in a flow of 20% $O_2$/He UHP grade at a rate of 100 cc/minute and with a temperature ramp of 10° C./minute up to a maximum temperature of 650° C. The sample is held at this temperature for one hour, then purged with UHP grade helium for 15 minutes and cooled to the saturation temperature. The pretreatment is for removal of water and residual contaminants. The sample is saturated with anhydrous $NH_3$ at 150° C. using multiple pulses of $NH_3$ injected into He flowing at 40 cc/min. The minimum quantity of $NH_3$ used to saturate the sample is 50 cc. The excess ammonia is purged from the sample in flowing (40 cc/min) UHP grade helium for about 8 hours. The $NH_3$ is desorbed from the sample in a flow (40 cc/min) of UHP grade helium with a temperature ramp of 10° C./minute to a final temperature of about 605° C. All gases have been purified using appropriate gas purifiers. The $NH_3$ desorbed is detected with a Thermal Conductivity Detector. The detector response is converted to moles of $NH_3$ using the detector response obtained at the beginning of the experiment. The integrated results are reported by integration of the temperature range of interest and reported as mmoles $NH_3$/g sample. An example of the first zeolite is UZM-8.

The second zeolite having a silica to alumina molar ratio less than 8, and includes a rare earth element incorporated into the zeolitic framework in an amount greater than 16.5 wt %. The first zeolite component is in an amount between 10 and 90% by weight of the catalyst, and the second zeolite component is in an amount between 10 and 90% by weight. The zeolites are intermingled into single catalyst particles. An example of the second zeolite is a rare earth substituted X zeolite, Y zeolite, or a zeolite having an EMT/FAU intergrowth. The incorporation of rare earth exchanged ions in a low ratio zeolite reduces the acidity due to an increase in the number of framework alumina at low ratios, and also reduces geometric space in the supercage. The reduced acidity and reduced space significantly suppresses the isomerization and cracking pathways, while the leaving the primary alkylation reaction unaffected. This decreases the undesired side reactions that reduce the amount and quality of the LAB product. This is contrary to what one would expect, as it has been found that incorporating or leaving some alkali or alkaline earth cations in the catalyst significantly improves the catalyst performance. This is especially true with respect to the performance around the linearity of the alkylbenzene, and the retention of linearity as the operating temperatures are increased. Normally, the alkali or alkaline earth cations are removed because without the rare earth exchange, the alkali or alkaline earth cations are detrimental to the catalyst life and regenerability.

The alkylation reaction zone may contain at least 2, or at least 3, and most frequently between about 3 and 10, reaction zones in series to which a portion of the aliphatic feedstock is fed. Often a trim alkylation reaction zone follows the series to react residual olefin in the effluent from the last reaction zone in series. The reaction zones may be in a common vessel or in separate vessels. The reaction zones may be the same or different sizes. Additional reaction zones may be used in parallel.

In common commercial configurations for alkylbenzene, the refining assembly comprises a distillation assembly that recovers essentially all the benzene from the alkylation effluent and provides a relatively pure benzene stream as the overhead. The bottoms stream from this distillation assembly would then be passed to a distillation assembly to separate as the overhead, paraffins and unreacted olefins, and the bottoms from this second distillation assembly would be fed to a heavies distillation assembly where the alkylbenzene product is contained in the overhead. If desired, a finishing column may be used to further purify the alkylbenzene, especially after a clay treatment to remove color formers.

In further detail for purposes of illustration, the benzene distillation is generally conducted with a bottoms temperature of less than about 300° C., preferably less than about 275° C., usually between about 230° C. and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column used for benzene distillation may contain any convenient packing or distillation trays, but most often trays such as sieve and bubble trays, are used. Often the assembly provides at least about 5 theoretical plates, for example, 6 to 70, or 20 to 50. The reflux ratio is often in the range of about 2:1 to 1:10, or about 1.5:1 to 1:5. The bottoms stream from the benzene distillation generally contains less than about 1000 ppmw, or less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., or less than about 275° C., usually between about 250° C. and 275° C., and at a pressure at which overhead is provided of between about 5 and 110 kPa absolute, or between about 10 and 50 kPa absolute. The column may contain any convenient packing or distillation trays, but most often sieve trays are used. Often the paraffins distillation assembly provides at least about 5 theoretical plates, or about 7 to about 20. The reflux ratio is often in the range of about 3:1 to 1:10, or about 1:1 to 1:3. The bottoms stream from the paraffins distillation generally contains less than about 5000, or less than about 500, parts by million by weight (ppmw) paraffins and less than about 10, often less than about 1, ppmw benzene. The paraffins distillation may occur in a single column, or two or more distinct columns may be used.

The heavy alkylbenzene distillation is generally conducted with a bottoms temperature of less than about 300° C., or less than about 275° C., usually between about 250° C. and 275° C., and at a pressure of between about 0.5 and 30 kPa absolute, or between about 1 and 5 kPa absolute. The column may contain any convenient packing or distillation trays, but most often structured packing is used. Often the heavy alkylbenzene distillation assembly provides at least about 5 theoretical plates, for example 10 to 30, or 10 to 20. The reflux ratio is often in the range of about 2:1 to 1:5, or about 0.2:1 to 1:1. The overhead from the heavy alkylbenzene distillation generally contains less than about 1000 ppmw, or less than about 100 ppmw, and sometimes less than about 50 ppmw, total heavy alkylbenzene.

The refining system may contain additional distillation zones, e.g., to recover additional alkylbenzene from heavy alkylbenzene.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for producing alkylaromatic compounds comprising:
    contacting an aromatic compound and an olefin in an alkylation reaction zone under alkylation conditions in the presence of an alkylation catalyst to produce an alkylation product containing monoalkylaromatic compounds, dialkylaromatic compounds, and unreacted aromatic compound;
    separating the alkylation product in a separation zone into an unreacted aromatic fraction and a fraction containing the monoalkylaromatic compounds and the dialkylaromatic compounds;
    regenerating a spent alkylation reaction zone by passing an aromatic compound stream through the spent alkylation zone at a regeneration temperature above an alkylation temperature to provide a regeneration aromatic compound stream; and
    introducing at least about 80 wt % of the regeneration aromatic compound stream directly into the alkylation zone, the regeneration aromatic compound stream being at the alkylation temperature.

2. The process of claim 1 wherein regenerating a spent alkylation reaction zone comprises heating the spent alkylation zone from the alkylation temperature to the regeneration temperature, maintaining the spent alkylation zone at the regeneration temperature for a period of time, and cooling the spent alkylation zone from the regeneration temperature to the alkylation temperature.

3. The process of claim 2 wherein heating the spent alkylation zone from the alkylation temperature to the regeneration temperature takes about 8 hr, wherein the spent alkylation zone is maintained at the regeneration temperature for about 8 hr, and wherein cooling the spent alkylation zone from the regeneration temperature to the alkylation temperature takes about 8 hr.

4. The process of claim 1 wherein at least about 50 wt % of the regeneration aromatic compound stream is introduced into the alkylation zone.

5. The process of claim 1 further comprising:
    separating the fraction containing the monoalkylaromatic compounds and the dialkylaromatic compounds into a monoalkylaromatic compound stream and a dialkylaromatic compound stream;
    introducing the dialkylaromatic compound stream and a second aromatic compound into a transalkylation reaction zone under transalkylation conditions to produce a transalkylation product containing monoalkylaromatics, unreacted dialkylaromatics, and unreacted second aromatic compound;
    introducing a second portion of the regeneration aromatic compound stream into the transalkylation reaction zone as at least a portion of the second aromatic compound.

6. The process of claim 5 wherein the second portion of the regeneration aromatic compound stream comprises at least about 50 wt % of a remainder of the regeneration aromatic compound stream, the remainder of the regeneration aromatic compound stream being the regeneration aromatic compound stream minus the portion introduced into the alkylation zone.

7. The process of claim 1 further comprising introducing a third portion of the regeneration aromatic compound stream into the separation zone.

8. The process of claim 1 wherein the alkylation temperature is in a range of about 120° C. to about 150° C., and the regeneration temperature is in a range of about 160° C. to about 250° C.

9. The process of claim 1 wherein the alkylation temperature is in a range of about 130° C. to about 140° C., and the regeneration temperature is in a range of about 180° C. to about 250° C.

10. The process of claim 1 wherein regenerating the spent alkylation reaction zone takes place at a pressure in a range of 1.300 MPa(g) to about 7.000 MPa(g).

11. The process of claim 1 wherein the alkylation catalyst is selected from mordenite, ZSM-4, ZSM-12, ZSM-20, ZSM-38, offretite, gmelinite, beta, NU-87, UZM-8, MCM-22, MCM-36, MCM-49, zeolite Y, zeolite X, gottardite, MOR, MWW, FAU, RE-Y, NES, ZDA-2, DA-114, or combinations thereof.

12. A process for producing alkylaromatic compounds comprising:
    contacting an aromatic compound and an olefin in an alkylation reaction zone under alkylation conditions in the presence of an alkylation catalyst to produce an alkylation product containing monoalkylaromatic compounds, dialkylaromatic compounds, and unreacted aromatic compound;

separating the alkylation product in a separation zone into an unreacted aromatic fraction and a fraction containing the monoalkylaromatic compounds and the dialkylaromatic compounds;

regenerating a spent alkylation reaction zone by passing an aromatic compound stream through the spent alkylation zone while heating the spent alkylation zone from an alkylation temperature to a regeneration temperature, maintaining the spent alkylation zone at the regeneration temperature for a period of time, and cooling the spent alkylation zone from the regeneration temperature to the alkylation temperature to provide a regeneration aromatic compound stream;

introducing at least about 80 wt % of the regeneration aromatic compound stream directly into the alkylation zone, the regeneration aromatic compound stream being at the alkylation temperature.

13. The process of claim 12 wherein heating the spent alkylation zone from the alkylation temperature to the regeneration temperature takes about 8 hr, wherein the spent alkylation zone is maintained at the regeneration temperature for about 8 hr, and wherein cooling the spent alkylation zone from the regeneration temperature to the alkylation temperature takes about 8 hr.

14. The process of claim 12 wherein at least about 50 wt % of the regeneration aromatic compound stream is introduced into the alkylation zone.

15. The process of claim 12 further comprising:

separating the fraction containing the monoalkylaromatic compounds and the dialkylaromatic compounds into a monoalkylaromatic compound stream and a dialkylaromatic compound stream;

introducing the dialkylaromatic compound stream and a second aromatic compound into a transalkylation reaction zone under transalkylation conditions to produce a transalkylation product containing monoalkylaromatics, unreacted dialkylaromatics, and unreacted second aromatic compound;

introducing a second portion of the regeneration aromatic compound stream into the transalkylation reaction zone as at least a portion of the second aromatic compound.

16. The process of claim 15 wherein the second portion of the regeneration aromatic compound stream comprises at least about 50 wt % of a remainder of the regeneration aromatic compound stream, the remainder of the regeneration aromatic compound stream being the regeneration aromatic compound stream minus the portion introduced into the alkylation zone.

17. The process of claim 12 further comprising introducing a third portion of the regeneration aromatic compound stream into the separation zone.

18. The process of claim 12 wherein the alkylation temperature is in a range of about 120° C. to about 150° C., and the regeneration temperature is in a range of about 160° C. to about 250° C.

19. The process of claim 12 wherein regenerating a spent alkylation reaction zone takes place at a pressure in a range of 2.758 MPa to about 4.137 MPa.

20. The process of claim 12 wherein the alkylation catalyst is selected from mordenite, ZSM-4, ZSM-12, ZSM-20, ZSM-38, offretite, gmelinite, beta, NU-87, UZM-8, MCM-22, MCM-36, MCM-49, zeolite Y, zeolite X, gottardite, MOR, MWW, FAU, RE-Y, NES, ZDA-2, DA-114, or combinations thereof.

* * * * *